United States Patent [19]

Kutter et al.

[11] 4,021,558

[45] May 3, 1977

[54] 1,3-DIOXO-2-[(METHOXYPHENETHYL-AMINO)-ALKYL]-4,4-DIMETHYL-ISOQUINOLINES AND SALTS THEREOF USEFUL AS HYPOTENSIVE AGENTS

[75] Inventors: Eberhard Kutter; Volkard Austel, both of Biberach an der Riss; Wolfgang Eberlein, Mettenberg, Biberach; Joachim Heider, Warthausen-Oberhofen, all of Germany

[73] Assignee: Boehringer Ingelheim GmbH, Ingelheim am Rhein, Germany

[22] Filed: Jan. 22, 1976

[21] Appl. No.: 651,568

Related U.S. Application Data

[63] Continuation-in-part of Ser. No. 503,072, Sept. 4, 1974, Pat. No. 3,948,898.

[30] Foreign Application Priority Data

Sept. 8, 1973 Germany .......................... 2345422
Sept. 8, 1973 Germany .......................... 2345423

[52] U.S. Cl. .......................... 424/258; 260/268 BA
[51] Int. Cl.² .......................... A61K 31/47
[58] Field of Search ............ 424/258; 260/268 BQ, 260/288 R

[56] References Cited

UNITED STATES PATENTS

| 3,726,875 | 4/1973 | Kadin ............ 260/268 BQ |
| 3,753,994 | 8/1973 | Diana ............ 424/258 |
| 3,778,440 | 12/1973 | Simpson ............ 424/258 |
| 3,870,721 | 3/1975 | Archibald et al. ............ 260/268 D |

OTHER PUBLICATIONS

Chemical Abstracts, vol. 73, 45304a (1970).

*Primary Examiner*—Albert T. Meyers
*Assistant Examiner*—Daren M. Stephens
*Attorney, Agent, or Firm*—Hammond & Littell

[57] ABSTRACT

Compounds of the formula

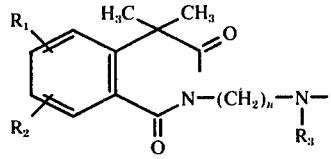

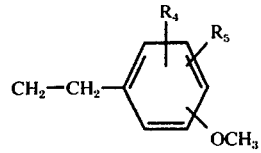

wherein $R_1$ is hydrogen, halogen, methoxy or methylthio,
$R_2$ is hydrogen or methoxy,
$n$ is 2 or 3,
$R_3$ is hydrogen or methyl, and
$R_4$ and $R_5$, which may be identical to or different from each other, are each hydrogen or methoxy, and non-toxic, pharmacologically acceptable acid addition salts thereof; the compounds as well as the salts are useful as hypotensives, sedatives, antiarrhythmics and bradycardiacs.

4 Claims, No Drawings

1,3-DIOXO-2-[(METHOXYPHENETHYL-AMINO)-ALKYL]-4,4-DIMETHYL-ISOQUINOLINES AND SALTS THEREOF USEFUL AS HYPOTENSIVE AGENTS

This is a continuation-in-part of copending application Ser. No. 503,072 filed Sept. 4, 1974, now U.S. Pat. No. 3,948,898 granted April 6, 1976.

This invention relates to novel 1,3-dioxo-2-[(methoxy-phenethyl-amino)-alkyl]-4,4-dimethyl-isoquinolines and their non-toxic acid addition salts, as well as to methods of preparing these compounds.

More particularly, the present invention relates to a novel class of isoquinoline derivatives represented by the formula

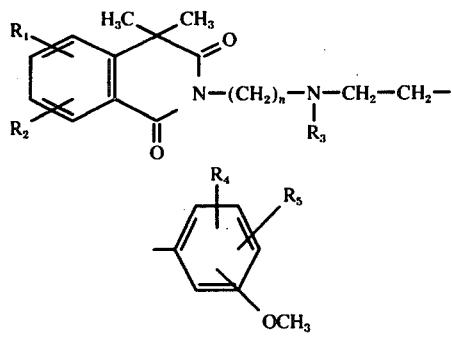

(I)

wherein
$R_1$ is hydrogen, halogen, methoxy or methylthio,
$R_2$ is hydrogen or methoxy,
n is 2 or 3,
$R_3$ is hydrogen or methyl, and
$R_4$ and $R_5$, which may be identical to or different from each other, are each hydrogen or methoxy, and non-toxic, pharmacologically acceptable acid addition salts thereof.

The compounds embraced by formula I may be prepared by the following methods:

Method A

By reacting a compound of the formula

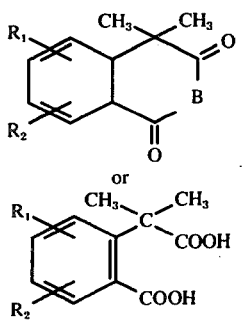

(II)

or (IIa)

wherein
$R_1$ and $R_2$ have the same meanings as in formula I, and
B is oxygen, imino or substituted imino, with an amine of the formula

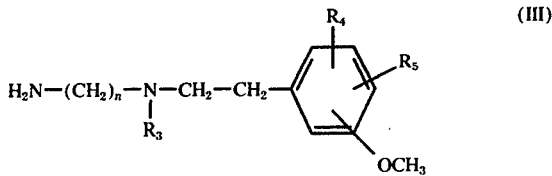

(III)

wherein $n$, $R_3$, $R_4$ and $R_5$ have the same meanings as in formula I, or an acid addition salt thereof.

The reaction is preferably carried out in the presence of a solvent, such as glycol, or without a solvent in the molten state, at temperatures from about 50° to 250° C. The addition of a base, such as potassium tert.butylate is of advantage, especially if the compound of the formula III is used in the form of an acid addition salt.

Method B

By reacting a N-alkyl-isoquinoline-dione of the formula

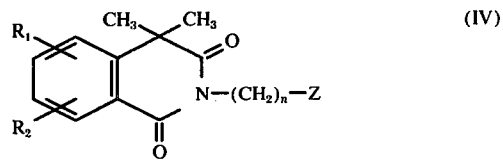

(IV)

wherein
$R_1$, $R_2$ and n have the same meanings as in formula I, and
Z is a nucleophilically easily exchangeable group, preferably chlorine, bromine, iodine, alkylsulfonyloxy or arylsulfonyloxy, such as toluenesulfonyloxy,
with an amine of the formula

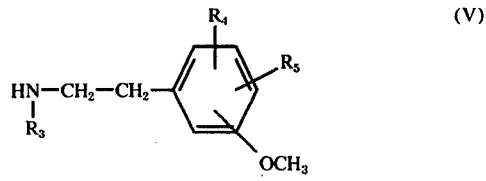

(V)

wherein $R_3$, $R_4$ and $R_5$ have the same meanings as in formula I.

The reaction is preferably carried out in the presence of a solvent, such as in methanol, ether, tetrahydrofuran, methylformamide, dimethylformamide, dimethylsulfoxide or benzene, and advantageously at temperatures between −50° and 250° C, depending on the reactivity of Z. The presence of an acid binding agent, such as an alcoholate, metal hydroxide, metal oxide or metal carbonate, is of advantage.

Method C

By reacting a homophthalimide of the formula

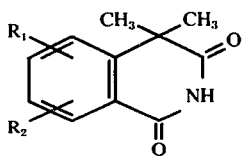

wherein $R_1$ and $R_2$ have the same meanings as in formula I, or a metal salt, preferably an alkali metal salt thereof, with a substituted amine of the formula

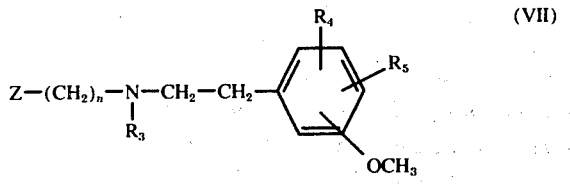

wherein Z, n, $R_3$, $R_4$ and $R_5$ have the meanings previously defined.

The reaction is preferably carried out in the presence of an acid binding agent, such as an alkali metal alcoholate, a metal oxide, metal hydroxide or metal carbonate, and advantageously in the presence of a solvent, such as methanol, isopropanol, dimethylformamide or dimethylsulfoxide, at temperatures between 0° C and the boiling point of the solvent which is used. If an alkali metal salt of the homophthalimide of the formula VI is used as the starting compound, the presence of an acid binding agent is not required.

The starting compounds embraced by formulas II through VII are either described in the literature or may be prepared by processes described in the literature.

The compounds of the formula I are organic bases and therefore form addition salts with acids. Examples of non-toxic, pharmacologically acceptable acid addition salts are those formed with mineral acids, such as hydrochloric acid, hydrobromic acid, hydroiodic acid, hydrofluoric acid, nitric acid, sulfuric acid or phosphoric acid; or organic acids, such as acetic acid, propionic acid, butyric acid, malonic acid, succinic acid, maleic acid, fumaric acid, malic acid, tartaric acid, citric acid, benzoic acid, p-hydroxybenzoic acid, p-aminobenzoic acid, salicylic acid, acetyl-salicylic acid, phthalic acid, terephthalic acid, ascorbic acid, methanesulfonic acid, ethanephosphonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

1-[4,4-Dimethyl-7-methoxy-1,3-dioxo-(2H,4H)-isoquinolin-2-yl]-2-[2-(3,4-dimethoxy-phenyl)-ethylamino]-ethane and its hydrochloride by method B.

A mixture of 8.5 gm of 2-(2-chloro-ethyl)-4,4-dimethyl-7-methoxy-1,2,3,4-tetrahydro-isoquinoline-dione-(1,3) and 13.6 gm of 3,4-dimethoxyphenyl-ethylamine was heated for 4 hours on an oil bath at a bath temperature of 180° C. Subsequently, water was added. The mixture was extracted with chloroform, and the chloroform phase was washed with water, dried and evaporated. Then, the raw free base reaction product was purified by column chromatography (silicagel column; chloroform/methanol = 95/5), the main fraction was isolated, and the hydrochloride was precipitated by addition of ethereal hydrochloric acid, yielding the compound of the formula having a melting point of 263°–265° C after recrystallization from ethanol.

EXAMPLE 2

1-[4,4-Dimethyl-1,3-dioxo-(2H,4H)-isoquinolin-2-yl]-2-[2-(3, 4-dimethoxy-phenyl)-ethylamino]-ethane and its hydrochloride, m.p. 148°–151° C after recrystallization from ethanol, were prepared analogous to Example 1 from 2-(2-chloro-ethyl)-4,4-dimethyl-1,2,3,4-tetrahydro-isoquinoline-dione-(1,3) and 3,4-dimethoxy-phenyl-ethylamine.

EXAMPLE 3

1-[4,4-Dimethyl-7-methoxy-1,3-dioxo-(2H,4H)-isoquinolin-2-yl]-2-[N-methyl-2-(3,4-dimethoxyphenyl)-ethylamino]-ethane and its hydrochloride, m.p. 138°–140° C, were prepared analogous to Example 1 from N-methyl-N-[2-(3,4-dimethoxy-phenyl)-ethyl]-amine and 2-(2-chloro-ethyl)-4,4-dimethyl-7-methoxy-1,2,3,4-tetrahydro-isoquinoline-dione-(1,3).

EXAMPLE 4

1-[4,4-Dimethyl-1,3-dioxo-(2H,4H)-isoquinolin-2-yl]-3-[N-methyl-N-(2-(3,4-dimethoxy-phenyl)-ethyl)-amino]-propane, a viscous oil, was prepared analogous to Example 1 from 2-(3-chloro-propyl)-4,4-dimethyl-1,2,3,4-tetrahydroisoquinoline-dione-(1,3) and N-methyl-2-(3,4-dimethoxy-phenyl)-ethylamine.

EXAMPLE 5

1-[4,4-Dimethyl-7-methoxy-1,3-dioxo-(2H,4H)-isoquinolin-2-yl]-3-[N-methyl-2-(3,4-dimethoxy-phenyl)-ethylamino]-propane, a viscous oil, was prepared analogous to Example 1 from 2-(3-chloro-propyl)-4,4-dimethyl-7-methoxy-1,2,3,4-tetrahydroisoquinoline-dione-(1,3) and N-methyl-2-(3,4-dimethoxy-phenyl)-ethylamine.

EXAMPLE 6

1-[4,4-Dimethyl-7-methoxy-1,3-dioxo-(2H,4H)-isoquinolin-2-yl]-3-[2-(3,4,5-trimethoxy-phenyl)-ethylamino]-propane and its hydrochloride, m.p. 157°–159° C after recrystallization from isopropanol, were prepared analogous to Example 1 from 2-(3,4,5-trimethoxy-phenyl)-ethylamine and 2-(3-chloro-propyl)-4,4-dimethyl-7-methoxy-1,2,3,4-tetrahydro-isoquinoline-dione-(1,3).

EXAMPLE 7

1-[4,4-Dimethyl-7-methoxy-1,3-dioxo-(2H,4H)-isoquinolin-2-yl]-3-[2-(4-methoxy-phenyl)-ethylamino]-propane and its hydrochloride, m.p. 175°–176° C after recrystallization from isopropanol, were prepared analogous to Example 1 from 2-(3-chloro-propyl)-4,4-dimethyl-7-methoxy-1,2,3,4-tetrahydroisoquinoline-dione-(1,3) and 2-(4-methoxy-phenyl)-ethylamine.

EXAMPLE 8

1-[4,4-Dimethyl-1,3-dioxo-(2H,4H)-isoquinolin-2-yl]-3-[2-(3,4-dimethoxy-phenyl)-ethylamino]-propane and its hydrochloride, m.p. 162°–165° C after recrystallization from isopropanol, were prepared analogous to Example 1 from 2-(3-chloro-propyl)-4,4-dimethyl-1,2,3,4-tetrahydroisoquinoline-dione-(1,3) and 2-(3,4-dimethoxy-phenyl)-ethylamine.

EXAMPLE 9

1-[4,4-Dimethyl-7-methoxy-1,3-dioxo-(2H,4H)-isoquinolin-2-yl]-3-[2-(3,4-dimethoxy-phenyl)-ethylamino]-propane and its hydrochloride by method A.

a.
2-[2-(3,4-Dimethoxy-phenyl)-ethylamino]-1-cyanoethane 54.5 gm of 2-(3,4-dimethoxy-phenyl)-ethylamine were dissolved in 100 ml of methanol, a solution of 16.2 gm of acrylonitrile in 50 ml of methanol was added dropwise at 50° C, and the mixture was stirred for 1 hour at 50° C. After evaporation of the methanol, the raw reaction product thus obtained was used without further purification in the next step.

b.
1-[2-(3,4-Dimethoxy-phenyl)-ethylamino]-3-aminopropane

The raw reaction product (70.3 gm) obtained in the preceding step was taken up in 1.3 liters of methanolic ammonia and the mixture was hydrogenated in an autoclave with presence of Raney nickel as the catalyst at 80° C and 50 atmospheres, yielding the above named 1,3-diamino-propane having a boiling point of 168°–173° C at 1 mm Hg.

c. 13.2 gm of 4,4-dimethyl-7-methoxy-1,2,3,4-tetrahydro-isochroman-dione-(1,3) and 14.3 gm of 1-[2-(3,4-dimethoxy-phenyl)-ethylamino]-3-amino-propane were boiled in 250 ml of toluene for 5 hours in an apparatus equipped with a water trap. After cooling, the hydrochloride was precipitated from the reaction solution with ethereal hydrochloric acid, and the oily product was recrystallized from ethanol, yielding 1-[4,4-dimethyl-7-methoxy-1,3-dioxo-(2H,4H)-isoquinolin-2-yl]-3-[2-(3,4-dimethoxy-phenyl)-ethylamino]-propane hydrochloride having a melting point of 191°–193° C.

EXAMPLE 10

1-[4,4-Dimethyl-6,7-dimethoxy-1,3-dioxo-(2H,4H)-isoquinolin-2-yl]-3-[2-(3,4-dimethoxy-phenyl)-ethylamino]-propane and its hydrochloride, m.p. 98°–101° C after recrystallization from ethyl acetate, were prepared analogous to Example 9 from 4,4-dimethyl-6,7-dimethoxy-1,2,3,4-tetrahydro-isochroman-dione-(1,3) and 1-[2-(3,4-dimethoxy-phenyl)-ethylamino]-3-amino-propane.

EXAMPLE 11

1-[4,4-Dimethyl-6,7-dimethoxy-1,3-dioxo-(2H,4H)-isoquinolin-2-yl]-3-[N-methyl-2-(3,4-dimethoxy-phenyl)-ethylamino]-propane and its hydrochloride, m.p. 167°–168° C, were prepared analogous to Example 9 from 4,4-dimethyl-6,7-dimethoxy-1,2,3,4-tetrahydro-iso-chroman-dione-(1,3) and 1-[N-methyl-2-(3,4-dimethoxy-phenyl)-ethylamino]-3-amino-propane.

EXAMPLE 12

1-[4,4-Dimethyl-7-methylmercapto-1,3-dioxo-(2H,4H)-isoquinolin-2-yl]-3-[2-(3,4-dimethoxy-phenyl)-ethylamino]-propane and its hydrochloride, m.p. 133°–135° C after recrystallization from ethanol, were prepared analogous to Example 9 from 4,4-dimethyl-7-methylmercapto-1,2,3,4-tetrahydro-isochroman-dione-(1,3) and 1-[2-(3,4-dimethoxy-phenyl)-ethylamino]-3-amino-propane.

EXAMPLE 13

1-[4,4-Dimethyl-7-chloro-1,3-dioxo-(2H,4H)-isoquinolin-2-yl]-3-[2-(3,4-dimethoxy-phenyl)-ethylamino]-propane and its hydrochloride, m.p. 222°–226° C after recrystallization from ethanol, were prepared analogous to Example 9 from 4,4-dimethyl-7-chloro-1,2,3,4-tetrahydro-isochromandione-(1,3) and 1-[2-(3,4-dimethoxy-phenyl)-ethylamino]-3-amino-propane.

The compounds embraced by formula I and their nontoxic acid addition salts have useful properties; more particularly, they exhibit mainly hypotensive activity as well as bradycardiac, antiarrhythmic and sedative activities in warm blooded animals, such as dogs.

The hypotensive activity of the compounds of the formula I and their non-toxic acid addition salts was ascertained in 2 to 4 mongrel dogs of male and female sex (body weight between 14 and 23 kg) under chloralose-urethane-nambutal anesthesia (54 + 270 + 10 mgm/kg i.v.). The test compounds were injected intravenously into the vena saphena in aqueous solution. The arterial bloodpressure was measured before and after administration in the arteria femoralis by means of a Stathan-pressure transducer and registered on a Grass-polygraph.

The following table shows illustrative, representative results obtained from these tests, where A = 1-[4,4-dimethyl-7-methoxy-1,3-dioxo-(2H,4H)-isoquinolin-2-yl]-3-[2-(3,4-dimethoxy-phenyl)-ethylamine]-propane hydrochloride.

| Compound | Dose mgm/kg i.v. | Decrease of bloodpressure mm Hg syst./diast. | Duration of activity in minutes |
| --- | --- | --- | --- |
| A | 0.5 | −32/−36 | 35 |
| A | 1.0 | −36/−40 | 40 |

The acute toxicity of the compounds was tested in mice (observation time: 14 days) after oral application. The LD$_{50}$ was calculated from the percentage of the animals which died within the observation time after application of varying doses [see J. Pharmacol. exper. Therap. 96,99 (1949)]:

| Compound | LD$_{50}$ mgm/kg p.o. |
| --- | --- |
| A | 775 |

For pharmaceutical purposes the compounds of the formula I or their non-toxic acid addition salts are administered to warm-blooded animals perorally or parenterally as active ingredients in customary dosage unit compositions, that is, compositions in dosage unit from consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.3 to 5.0 mgm/kg body weight, preferably 0.4 to 3.4 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 14

Tablets

The tablet composition is compounded from the following ingredients:

| | | |
| --- | --- | --- |
| 1-[4,4-Dimethyl-7-methoxy-1,3-dioxo-(2H,4H)-isoquinolin-2-yl]-3-[2-(3,4-dimethoxy-phenyl)-ethylamino]-propane hydrochloride | 100.0 | parts |
| Lactose | 50.0 | " |
| Polyvinylpyrrolidone | 5.0 | " |
| Carboxymethyl cellulose | 19.0 | " |
| Magnesium stearate | 1.0 | " |
| Total | 175.0 | parts |

Preparation:

The isoquinoline compound and the lactose are intimately admixed with each other, the mixture is homogeneously moistened with an aqueous solution of the polyvinylpyrrolidone, the moist mass is granulated by passing it through a screen, and the granulate is dried. The dry granulate is then admixed with the remaining ingredients, and the composition is compressed into 175 mgm-tablets in a conventional tablet making machine. Each tablet contains 100 mgm of the isoquinoline compound and is an oral dosage unit composition with effective hypotensive action.

EXAMPLE 15

Coated pills

The pill core composition is compounded from the following ingredients:

| | | |
| --- | --- | --- |
| 1-[4,4-Dimethyl-1,3-dioxo-(2H,4H)-isoquinolin-2-yl]-2-[2-(3,4-dimethoxy-phenyl)-ethylamino]-ethane hydrochloride | 50.0 | parts |
| Corn starch, dry | 20.0 | " |
| Soluble starch | 2.0 | " |
| Carboxymethyl cellulose | 7.0 | " |
| Magnesium stearate | 1.0 | " |
| Total | 80.0 | parts |

Preparation:

The isoquinoline compound and the corn starch are admixed with each other, the mixture is moistened with an aqueous solution of the soluble starch and then granulated by passing it through a screen, the granulate is dried and admixed with the remaining ingredients, and the composition is compressed into 80 mgm-pill cores which are subsequently coated with a thin shell consisting essentially of a mixture of sugar and talcum. The coated pills are finally polished with beeswax. Each coated pill contains 50 mgm of the isoquinoline compound and is an oral dosage unit composition with effective hypotensive action.

EXAMPLE 16

Suppositories

The suppository composition is compounded from the following ingredients:

| | | |
| --- | --- | --- |
| 1-[4,4-Dimethyl-1,3-dioxo-(2H,4H)-isoquinolin-2-yl]-3-[2-(3,4-dimethoxy-phenyl)-ethylamino]-propane hydrochloride | 150.0 | parts |
| Suppository base (e.g. cocoa butter) | 1550.0 | " |
| Total | 1700.0 | parts |

Preparation:

The suppository base is melted, the isoquinoline compound is homogeneously blended into the molten mass with the aid of an immersion homogenizer, and 1700 mgm-protions of the composition are poured into cooled suppository molds and allowed to harden therein. Each suppository contains 150 mgm of the isoquinoline compound and is a rectal dosage unit composition with effective hypotensive action.

EXAMPLE 17

Aqueous suspension

The suspension is compounded from the following ingredients:

| | | |
| --- | --- | --- |
| 1-[4,4-Dimethyl-1,3-dioxo-(2H,4H)-isoquinolin-2-yl]-2-[2-(3,4-dimethoxy-phenyl)-ethylamino]-ethane hydrochloride | 5.0 | parts |
| Carboxymethyl cellulose | 0.1 | " |
| Methyl p-hydroxy-benzoate | 0.05 | parts |
| Propyl p-hydroxy-benzoate | 0.01 | " |
| Sugar | 10.0 | " |
| Glycerin | 5.0 | " |
| Sorbitol, aqueous 70% solution | 20.0 | " |
| Flavoring | 0.3 | " |
| Distilled water q.s.ad | 100.0 | " |
| | | by vol. |

Preparation:

The distilled water is heated to 70° C, and the p-hydroxy-benzoates, the glycerin and the carboxymethyl cellulose are dissolved therein while stirring. The resulting solution is cooled to room temperature, the isoquinoline compound is homogenously suspended therein, and the sugar, the sorbitol solution and the flavoring are stirred in. Finally, the suspension is de-aerated by stirring in vacuo. 5 ml of the suspension contains 250 mgm of the isoquinoline compound and are an oral dosage unit composition with effective hypotensive action.

Analogous results are obtained when any of the other isoquinoline compounds embraced by formula I or a nontoxic acid addition salt thereof is substituted for the particular isoquinoline derivative in Examples 14 through 17. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

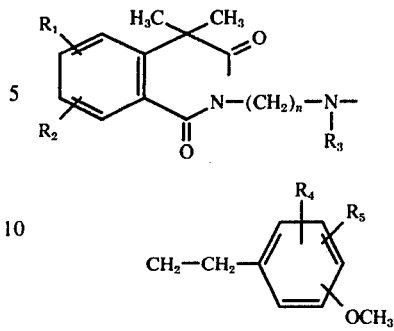

wherein
$R_1$ is hydrogen, halogen, methoxy or methylthio,
$R_2$ is hydrogen or methoxy,
$n$ is 2 or 3,
$R_3$ is hydrogen or methyl, and
$R_4$ and $R_5$ are each hydrogen or methoxy,
or a non-toxic, pharmacologically acceptable acid addition salt thereof.

2. A compound of claim 1, which is 1-[4,4-dimethyl-7-methoxy-1,3-dioxo-(2H,4H)-isoquinoline-2-yl]-3-[2-(3,4-dimethoxy-phenyl)-ethylamino]-propane or a non-toxic, pharmacologically acceptable acid addition salt thereof.

3. The method of lowering the blood pressure of a warm-blooded animal in need of such treatment, which comprises administering to said animal an effective hypotensive amount of a compound of claim 1.

4. A hypotensive pharmaceutical dosage unit composition consisting essentially of an inert pharmaceutical carrier and an effective hypotensive amount of a compound of claim 1.

* * * * *